United States Patent [19]

Kunkel

[11] Patent Number: 4,873,192
[45] Date of Patent: Oct. 10, 1989

[54] PROCESS FOR SITE SPECIFIC MUTAGENESIS WITHOUT PHENOTYPIC SELECTION

[75] Inventor: Thomas A. Kunkel, Durham, N.C.

[73] Assignee: The United States of America as represented by the Department of Health and Human Services, Washington, D.C.

[21] Appl. No.: 196,779

[22] Filed: May 18, 1988

Related U.S. Application Data

[63] Continuation of Ser. No. 15,316, Feb. 17, 1987, abandoned, which is a continuation of Ser. No. 623,923, Jun. 25, 1984, abandoned.

[51] Int. Cl.$^4$ .................. C12N 15/00; C12N 7/00; C12P 21/00; C12P 19/34
[52] U.S. Cl. .................................. 435/172.3; 435/6; 435/68; 435/91; 435/172.1; 435/317.1; 435/320; 935/10; 935/16; 536/27
[58] Field of Search ............. 435/6, 68, 91, 70, 172.1, 435/172.3, 317.1, 320; 536/27; 935/10, 16

[56] References Cited

U.S. PATENT DOCUMENTS 4,351,901  9/1982  Ball .................................... 435/91

OTHER PUBLICATIONS

Smith et al. (1981) in *Genetic Engineering*, ed. Setlow et al., vol. 3, pp. 1–32, Plenum Press.
Sagher et al. (1983) *Biochemistry*, vol. 22, pp. 4218–4226.
Zakour et al. (1982) *Nature*, vol. 295, pp. 708–710.
Messing (1983) in *Methods in Enzymology*, vol. 101, ed. Moldave, pp. 62–65.
Wagner et al. (1976) *Proc. National Acad. Sci. USA*, vol. 73, pp. 4135–4139.
Duncan et al. (1982) *J. Bacteriology*, vol. 151, pp. 750–755.
Shortle et al. (1978) *Proc. Nat'l. Acad. Sci. USA*, vol. 75, pp. 2170–2174.
Lu et al. (1983) *Proc. National Acad. Sci. USA*, vol. 80, pp. 4639–4643.
Lathe and Lecocq, *Genetic Engineering*, R. Williamson (ed.), Academic Press, NY, vol. 4, pp. 1–56 (1983).
Kunkel, PNAS, vol. 81, pp. 1494–1498 (1984).

*Primary Examiner*—Thomas G. Wiseman
*Assistant Examiner*—S. Seidman
*Attorney, Agent, or Firm*—John S. Roberts, Jr.; Mishrilal Jain

[57] ABSTRACT

The present invention discloses several DNA mutagenesis processes using a DNA template containing several uracil residues in place of thymine, which can be applied without selection techniques to produce altered DNA sequences with approximately 10-fold greater efficiency than current methods of site-specific mutagenesis.

This template has relatively normal coding potential in the in vitro reactions typical of standard site-directed mutagenesis protocols but is not biologically active upon transfection into a wild type (i.e., ung+) E. coli host cell. Expression of a desired change, present in the newly synthesized non-uracil-containing covalently closed circular complementary strand, is thus favored. The procedure has been applied to mutations introduced via both obligonucleotides and error-prone polymerization. The inclusion of two additional simple treatment steps before transfection results in a site-specific mutation frequency approaching 100%.

4 Claims, No Drawings

PROCESS FOR SITE SPECIFIC MUTAGENESIS WITHOUT PHENOTYPIC SELECTION

This application is a continuation of application Ser. No. 015,316, filed Feb. 17, 1987 which is a continuation of application No. 06/623,923, filed June 25, 1984.

The present invention is directed at increasing the efficiency of site specific mutagenesis by a process which utilizes a double stranded DNA molecule which is asymmetric for biological activity. That is, the desired DNA sequence alteration is placed in the strand which has normal biological activity and will survive the total process, while the other strand, containing the original sequence which is no longer desired, is made in such a way that it will not survive the process. Here this is accomplished by including uracil bases in the strand which is ultimately destroyed. The presence of this asymmetry for biological activity is a necessary feature of this invention. It is the presence of uracil in only one strand which makes the molecule asymmetric for biological activity, thus increasing efficiency.

MATERIAL INFORMATION DISCLOSURE

It is to be noted that the prior art believed to be most pertinent to this invention for material disclosure is as follows:

Sagher and Strauss, "Insertion of Nucleotides Opposite Apurinic/Apyrimidinic Sites in Deoxynucleic Acid During In Vitro Synthesis: Uniqueness of Adenine Nucleotides," *Biochemistry*, Vol. 22, pp. 4518–4526 (1983).

Zakour and Loeb, "Site Specific Mutagenesis by Error-Directed DNA Synthesis," *Nature*, 295: 708–710 (1982).

Smith and Gillam, *Genetic Engineering: Principles and Methods*, by J. K. Setlow and A. Hollaender, Vol. 3, pp. 1–32, Plenum Press, 1981.

Lathe and Lecocq, *Genetic Engineering*, R. Williamson (ed.), Academic Press, NY, Vol. 4, pp. 1–56.

Kunkel, *PNAS*, Vol. 81, pp. 1494–1498 (1984).

Kunkel, *PNAS*, "Rapid and Efficient Site-Specific Mutagenesis Without Phenotypic Selection," (submitted for publication). This article, hereby incorporated by reference, is the publication of the claimed invention.

UTILITY

The present invention discloses methods of site-specific mutagenesis of cloned genes which, in comparison to known mutagenesis techniques, show a marked increase in efficiency of 10 fold. These processes are applicable to at least two commercial uses: (1) changing regulatory regions in cloned genes, and (2) changing coding sequences in known genes. For example, the promoter sequence (a regulatory region) of human growth hormone is altered via the disclosed process in order to increase production of the hormone by 10 to 100 fold.

Examples of the second use are human oncogenes and herpes virus DNA polymerase. In the former, human oncogenes are changed so that the product(s) encoded by those genes are susceptible to a greater number of potential inhibitors used in preventive treatments. In the latter case, changes are made in the polymerase gene so that the gene product is more susceptible to inhibition by known inhibitors already in clinical use.

The present invention discloses several DNA mutagenesis processes using a DNA template containing several uracil residues in place of thymine, which result in approximately 10-fold greater efficiency compared to current methods of site-specific mutagenesis.

This template has relatively normal coding potential in the in vitro reactions typical of standard site-directed mutagenesis protocols but is not biologically active upon transfection into a wild type (i.e., ung+) *E. coli* host cell. Expression of a desired change, present in the newly synthesized non-uracil-containing covalently closed circular complementary strand, is thus favored. The procedure has been applied to mutations introduced via both oligonucleotides and error-prone polymerization. The inclusion of two additional simple treatment steps before transfection results in a site-specific mutation frequency approaching 100%.

BACKGROUND

Techniques for site-specific mutagenesis of cloned genes are well established; several variations are currently in use in many laboratories. Prior to the development of adequate recombinant DNA techniques, mutants could be obtained only by random mutagenesis requiring selection techniques specific for a particular phenotype. More modern techniques, however, provide scientists with other methods of altering DNA sequences by site-specific mutagenesis. Most of these techniques are summarized in Lathe, R. F. et al, *Genetic Engineering*, Academic Press, NY, Vol. 4, pp. 1–56 (1983). In essence, these techniques describe methods of manipulating DNA involving the transfer of DNA segments from one location to another. Such manipulation may permit the alteration of a DNA sequence in order to determine its function, or may permit the production of reagents with commercial or medical significance.

The present invention, an improvement on these techniques, is based on the discovery of three elements: (a) uracil exhibits the same normal coding potential as thymine [Warner et al, *J. Bacteriol.*, Vol. 145, pp. 687–695 (1981); and Kunkel, *PNAS*, Vol. 81, pp. 1494–1498 (1984)]; (b) uracil can be removed to create an abasic site, and in single strand DNA, an abasic site is lethal, i.e., biologically inactivated [Schaaper et al, *PNAS*, Vol. 78, pp. 1773–1777 (1981); and the Kunkel paper cited above]; and (c) the development of a uracil-containing DNA template [Sagher et al, *Biochemistry*, Vol. 22, pp. 4518–4526 (1983) and Tye et al, *PNAS*, Vol. 75, pp. 233–237 (1978)].

GENERAL DESCRIPTION

The above elements lay the groundwork for the present invention: a uracil-containing template DNA is hybridized to a complementary strand fragment containing the new DNA sequences. Following known procedures, the template and the complementary strand are transfected, transformed, or infected (depending on the procedure used) into *E. coli* (ung+) cells. *E. coli* ung+ cells inactivate the template DNA but do not inactivate the complementary strand containing the new DNA sequences. In short, this process preferentially produces the new DNA sequences' product. The real significance of this development, however, lies with the increased efficiency and decreased time involved. For example, known mutagenesis procedure may take up to several weeks to perform; the present invention can be completed in four hours.

In addition, the present invention is applicable to virtually all systems requiring DNA alteration or site-specific mutagenesis. For example, the process is effective when silent, unknown and/or non-selectable phenotypes are used as the new DNA sequences. This invention is also applicable to transformation techniques (inserting plasmids), transfection (inserting bacteriophage DNA), or infection (for insertion of packaged phage such as bacteriophage λ).

A uracil-containing template, which codes normally in the in vitro DNA synthesis needed to produce the desired change, but which is destroyed by repair pathways inside the normal cell, is needed to express the change. The result is an enhanced production of the desired phenotype in vivo concomitant with selection against the original phenotype (in the template strand). Although the uracil-containing template is preferred, other substitutes may be used s long as an asymmetry, with respect to biological activity, is formed between the complementary strand and the template DNA strand. The specific disclosure of the invention will further elucidate this point.

The complementary strand contains the DNA change desired by the practitioner. The present invention does not claim the creation or the specific nature of these changes, nor are all possible specific changes, made possible by modern technology, described here due to the vast number of variations known in the art. Accordingly, the essence of the present invention is not a particular DNA sequence alteration. It is, however, a new method of producing a product coded by a DNA sequence. Any known DNA sequence may be inserted using the system required by the inclusion of that DNA sequence. For example, a plasmid may be used as a template DNA in order to effectuate the desired DNA alteration or change. If a plasmid is used, the E. coli strain is *transformed* by the plasmid in subsequent process steps. However, if a bacteriophage is used, the subsequent process steps require *transfection* of the phage in an E. coli host. Additionally, several forms of oligonucleotides may be used as the complementary strand. In this case, the oligonucleotide may either contain the desired DNA change or the desired change may be attached (ligated or polymerized) to one end of the oligonucleotide.

Furthermore, the desired change is subject to the practitioner's choice. Although base substitution mutations are described here, the invention operates with other types of mutations, with any of the known cloning vector systems and known cloned genes. For example, the promoter sequence of human growth hormone can be altered in order to increase the production of the hormone—altering that promoter sequence using the present invention would significantly increase the production of hormone.

For simplicity sake, the present invention is described wherein the complementary strand is a restriction endonuclease fragment containing the desired change.

SPECIFIC DISCLOSURE

Preparation of the uracil-containing template

Single stranded viral DNA, the uracil-containing DNA template, is prepared from phage grown in an E. coli dut⁻ung⁻ strain. The process is described in Sagher et al, *Biochemistry*, Vol. 22, pp. 4518-4526 (1983). The procedure involves growing BW313 cells at 37° C. with vigorous shaking in YT medium (yeast extract 5 g/liter, tryptone 8 g/liter, NaCl 5 g/liter) supplemented with 20 ug/ml thymidine and 10 ug/ml deoxyadenosine. These cells are an E. coli strain (dut, ung, thi-1, relA, spoT1/F'lysA) obtained from Drs. D. Sagher and B. Strauss. At a cell density of $4 \times 10^8$/ml, the cells are centrifuged (15 min. at 2000 Xg), washed with YT, resuspended in fresh YT medium prewarmed to 37° and containing 0.25 μm/ml uridine (a uracil precursor), and shaken vigorously for 5 min. M13mp2 phage is then added at a multiplicity of infection of 5. Bacteriophage M13mp2, obtained from J. E. LeClerc, is a mutant containing a GC→CG transversion at position +82, and contains uracil in the DNA. M13mp2 is a preferred cloning vector, although other cloning vectors may be substituted. Also preferred but not required is the use of single-stranded DNA cloning vectors. BW313 and M13mp2 are then incubated overnight at 37°. After a single cycle of growth on BW313, relative phage survival is decreased to 0.1% when compared on an ung⁻ (BW313) versus an ung⁺ (CSH50) host. Phage obtained from this multiplication are used for a second cycle of growth, identical to the first, but producing phage exhibiting the relative survival values shown in Table 1 (Experiment 1). However, Example 3 shows that the second

TABLE 1

Survival of Uracil-containing M13mp2 Phage and DNA in ung⁻ and Wild Type E. coli Cells

| DNA Content | Titer ung⁻ host | Titer ung⁺ host | Survival (%) |
|---|---|---|---|
| Experiment 1 - Intact Phage Infection | | | |
| Wild type | $1.7 \times 10^{11}$ | $1.3 \times 10^{11}$ | 76.0 |
| Uracil-containing | $2.8 \times 10^{12}$ | $1.1 \times 10^7$ | 0.0006 |
| Experiment 2 - DNA Transfection | | | |
| Wild type | $3.0 \times 10^4$ | $2.7 \times 10^4$ | 90.0 |
| Uracil-containing | $2.0 \times 10^4$ | 0 | <0.005 |
| Wild type + glycosylase | $2.8 \times 10^4$ | $2.6 \times 10^4$ | 93.0 |
| Uracil-containing + glycosylase | 0 | 0 | <0.05* |

Preparation of phage and DNA, glycosylase treatment and transfection of competent cells are described in Specific Disclosure.
*This relative survival is calculated using the titer obtained with untreated uracil-containing DNA in the ung⁻ host ($2.0 \times 10^4$). The mutation frequency (for loss of α-complementation) was $6.5 \times 10^{-4}$ for wild type M13mp2 DNA and $12.0 \times 10^{-4}$ for uracil-containing M13mp2 DNA, when transfected into competent ung⁻ cells and plated.

cycle of growth may not be necessary. The culture is centrifuged at 5000 Xg and the phage ($10^{11}$/ml) are precipitated from the supernatant using 3% polyethylene glycol (PEG 8000), 0.5M NaCl. After centrifugation at 5000 Xg for 15 min, the phage pellet is resuspended in 50 mM Tris-HCl (pH 8.0), 1 mM EDTA, 100 mM NaCl, then phenol extracted twice, chloroform-isoamyl alcohol (24:1) extracted twice, ethanol precipitated and resuspended in 10 mM Tris-HCl (pH 8.0), 0.1 mM EDTA. The result is a single-stranded DNA template containing uracil in the DNA.

The complementary strand

As is mentioned above, the complementary strand and its hybridization to the DNA template are known quantities in the present invention. The strands that may be used are restriction restriction endonuclease fragment(s), oligonucleotides containing the desired DNA alteration, or oligonucleotides to which the desired DNA alteration is placed (ligated or polymerized). The critical quality is that a biological asymmetry must exist between the complementary and the DNA template strand. This asymmetry produces a situation in which the template is biologically active in vitro but is selected against or biologically inactive in vivo.

The description of the invention uses restriction endonuclease Pvu II, obtained from New England Biolabs. A 268-bp Pvu II restriction endonuclease fragment which spans positions −123 to +145 of the lacZ$_\alpha$ gene in M13mp2 is obtained using known methods. Four ug of this fragment is then hybridized to one ug of the uracil-containing template, also using well-known procedures. This hybridization results in a heteroduplex molecule containing a G(+):G(−) mismatch at site +82. In vitro DNA synthesis is then performed in order to form a covalently closed double-stranded heteroduplex molecule. The appropriate DNA synthesis reactions are performed in a 50 ul volume containing the primer-template, 20 mM Hepes (pH 7.8), 5 mM dithiothreitol, 10 mM MgCl$_2$, 200 mM rATP, 100 uM dATP, dTTP, dCTP and dGTP, 16 units of dUTPase, one unit of E. coli DNA polymerase I (large fragment) and, for the plus ligase condition, 10 units of T4 DNA ligase. Incubation was for 30 min. at 37° and reactions are terminated by adding EDTA to 15 mM.

Analysis of the product of this reaction on agarose gel indicates that approximately 20% of the input DNA is converted to covalently closed double-stranded circles. The remainder is either not ligated, only partially copied or remained uncopied.

Combining with an appropriate host cell

Transfection with this DNA mixture into E. coli host cells without selection against the template (i.e., in ung− host cells) produces a mutant phenotype frequency of 6.7%. This value is 50-fold above the background frequency, and is typical of current site-specific mutagenesis protocols before enrichment for only copied molecules.

Transfection of an aliquot of this same mixture of DNA molecules into competent ung+ cells gives a 51% mutation frequency, a 7.6-fold increase. As expected, in the absence of DNA synthesis, no survivors are observed in the ung+ transfection. In addition, the low yield of total survivors and mutants produced from in vitro reactions containing no ligase demonstrate that both arose primarily from covalently closed complementary strand circles.

The present invention is not limited by requiring transfection as a process step. Plasmids may be used to form the heteroduplex molecule, in which case the E. coli cells are transformed by the plasmid. Also, infection may be used, as is the case for packaged phage such as bacteriophage λ.

EXAMPLE 1

A variation of the process disclosed in the specific description was attempted in order to obtain an additional increase in mutation frequency. While transfection of the double-stranded heteroduplex clearly selects against the phenotype of the uracil-containing strand, it is possible that this methylated template strand could act to instruct mismatch correction within the complementary strand but in favor of the template phenotype, before the viral template strand is destroyed. Alternatively, the newly made complementary strand could be used in vivo as a template to repair the many abasic sites produced in the viral strand upon removal of uracil. Therefore, the product of the in vitro reaction was treated, before transfection, with either uracil glycosylase, or uracil glycosylase followed by alkali, to hydrolyze the AP apyrimidinic sites and disrupt hydrogen bonding.

Treatment of either normal or uracil-containing M13mp2 DNA was performed in a 25 ul reaction containing 10 mM Tris-HCl (pH 8.0), 1 mM EDTA, 4 ug of M13mp2 single-stranded DNA ($10^{12}$ molecules) and either buffer only or 100 ng ($2.5 \times 10^{12}$ molecules) of highly purified E. coli uracil glycosylase. Incubation was at 37° for 30 min. Reactions were then placed on ice and one ug each of the control and glycosylase-treated DNAs were used for transfection of competent cells, made from E. coli NR8051 (ung+) or NR8052 (ung−).

Alternatively, 200 ng of the copied, ligated DNA was treated with uracil glycosylase as described above, and then 100 ng of this DNA was mixed with alkali —0.2M NaOH (pH 12.8)—incubated at 37° for 5 minutes and neutralized; 25 ng were used for transfections.

These strategies are designed to produce, as the sole source of biological activity, covalently-closed complementary (i.e., mutant) single-stranded circles. The results of transfection of DNA treated in this way are shown in the last two lines of Table 2. As expected glycosylase treatment before transfection yielded a mutant frequency greater than 50% even in the ung− host, consistent with the concept that uracil removal, whether in vitro with the purified enzyme or in vivo, is responsible for the increase in frequency. More importantly, glycosylase followed by alkali treatment gave a mutation frequency of 81% (ung−) to 89% (ung+). Five light blue mutants were examined by DNA sequence analysis, and all five had the expected G→C change at position +82.

EXAMPLE 2

The experiments constituting this example were performed using deoxynucleoside triphosphates which had been preincubated with dUTPase to hydrolyze any dUTP contaminants in the commercial preparations of substrates. Any such dUTP could be incorporated into the complementary strand, destroying its selective advantage. However, in order to establish the general applicability of this technique, the effect of excluding the dUTPase treatment was also examined.

dUTPase treatment of substrates

Deoxynucleoside triphosphates were treated with highly purified dUTPase in a 50 μl reaction containing 5 mM each of dATP, dTTP, dCTP and dGTP, 30 mM Hepes (pH 7.8), and 800 units of dUTPase. Incubation was for 20 minutes at 22°, after which the dNTP substrates were used directly for the in vitro DNA synthesis reaction described in the specific disclosure. The results are shown in Table 2. Parallel reactions were performed with and without dUTPase and the products were transfected, without further treatment, into ung+ cells. Survival values were similar and the mutant frequencies were both 51%. This suggests that, using highly purified substrates, dUTPase treatment is not necessary. In subsequent experiments (Table 3) such treatment is omitted.

EXAMPLE 3

In a further attempt to improve the ease with which these processes can be applied, a parallel reaction was performed with a uracil-containing template prepared from phage produced in only one cycle of growth on the E. coli dut−ung− host (see the specific disclosure). The mutant frequency was 41%, in contrast to the 51% shown for the experiment in Table 2, consistent with the observation that relative survival (ung+/ung− host) of the (non-mutant) template is 100-fold greater with only one growth cycle. Since a 41% site-specific mutation frequency is more than adequate for many applications, a single growth cycle may often suffice.

EXAMPLE 4

Oligonucleotide-directed missense mutagenesis

In many instances site-specific mutations are introduced via oligonucleotides. The results of such an approach with a uracil-containing template are shown in Table 3 (Protocol 1). The mutation was introduced via the 15 base oligonucleotide (PL Biochemicals) complementary to nucleotides +76 to +90 of the lacZ$_\alpha$ gene in M13mp2. The 5'-OH termini were phosphorylated, then the 15-mer was hybridized at a 2:1 primer to template ratio to a (light blue) mutant M13mp2 template, containing a C at position +82, thus creating a C:C heteroduplex. Synthesis was performed as described in the Specific Disclosure, but at 0° for 15 min. followed by 16° for 120 min.

In this instance a proline codon is changed to an arginine codon through a C→G base change at position +82. A 15-base oligonucleotide containing the desired change was incorporated into a covalently closed complementary strand circle, using a uracil-containing M13mp2 template. The reaction was performed with E. coli DNA polymerase I, large fragment, at low temperature in an attempt to maximize utilization of the oligonucleotide and minimize strand displacement. Analysis of the products of the reaction by agarose gel electrophoresis demonstrated very little production of covalently closed circular double stranded DNA. This was reflected in low survival upon transfection into an ung+ host. Despite this limitation, the mutation frequency was 40%, clearly demonstrating the strong selection against the uracil-containing phenotype. Of four (blue) mutants examined, all four had the desired sequence change.

EXAMPLE 5

Site specific misincorporation mutagenesis to produce a nonsense codon

Uracil-containing templates can be used equally effectively to create specific mutations via misincorporation using an error prone DNA polymerase and a single dNTP substrate. Using a 17 base oligonucleotide, complementary to positions +59 to +75, hybridized to a wild type (i.e., blue) uracil-containing template, AMV polymerase was used to incorporate a single dTMP residue opposite a template C at position +58. This single base mutation was "fixed" by addition of the remaining three dNTP substrates to allow further chain elongation. Without any purification, T4 DNA polymerase and T4 DNA ligase were added to produce covalently closed double stranded molecules. Using 500 uM dNTPs, this reaction is highly efficient, typically converting 20-50% of the input template to the double-stranded form. Transfection of the products of this reaction usign ung+ host cells yielded colorless plaques at 53.4% efficiency. Sequence analysis of five colorless mutants confirmed the presence of the C→A change at the intended position in all five clones.

The experimental details are as follows:

Wild type (blue) uracil-containing M13mp2 template was primed with a 17-mer (P.L. Biochemicals) complementary to nucleotides +59 to +75 of the lac Z coding region. The desired site-specific change, a C→A single base change at position +58, was created by misincorporation of a T opposite a template C [a C(+):T(−) mismatch] using the error prone avian myeloblastosis virus polymerase and dTTP only. Reactions were performed as follows: To a 5 µl volume containing the oligonucleotide primed DNA (0.5 µg), 20 mM Hepes (pH 7.8), 10 mM MgCl$_2$, and 500 µM dTTP, was added 4 units of AMV DNA polymerase (Life Sciences, Inc.). After 10 min. at 37°, the remaining three dNTPs were added to 500 µM and incubation at 37° was continued for 5 min. The final additions were dithiothreitol to 2 mM, rATP to 200 uM, T4 DNA ligase, 5 units and T4 DNA polymerase (P.L. Biochemicals), 0.5 unit. Incubation was for 37° for 60 min., and the reactions were terminated by addition of EDTA to 15 mM.

EXAMPLE 6

Site specific mutagenesis without selection

In parallel with Example 5 (Protocol 2), a similar experiment was performed to incorporate dAMP opposite the template C at position +58 (Table 3, Protocol 3).

Protocol 3

The C→T change was produced as described in Protocol 2, except that the misincorporation of A opposite C at +58 was produced using AMV polymerase and dATP only. While this experiment was performed without selection, upon completion of the sequence analysis, a re-examination of the plates containing the mutant plaques showed that this change unexpectedly resulted in a very slight decrease in blue color intensity. The T→C change at position 72 was introduced using a 15-base oligonucleotide (Bethesda Research Laboratories) complementary to positions +73 to +87, AMV polymerase and dGTP only. As expected, this mutation was silent. In all cases the unfractionated products of the reactions were used to transfect competent ung+ host cells, then plated.

This protocol produces a C→T missense mutation coding for leucine rather than serine at amino acid 6 in the lacZ$_\alpha$ peptide. Amino acid changes in this region are expected to be silent, so this experiment was performed without color selection on the plates. Ten plaques, produced from transfection of the products of the in vitro reaction into ung+ cells, were subjected to DNA sequence analysis. Six had the desired change.

The ability to place a non-selectable or silent change at a desired position in a gene has many uses. As an example, under appropriate conditions, the run of the 4 thymine residues at positions +70 through +73 in the lacZ$_\alpha$ coding sequence represents a mutational "hot-spot" for frameshift mutations. To facilitate future studies with this DNA target it was desirable to alter the DNA sequence without altering the phenotype (dark blue color). This has been done by changing a T to a C at position +72. This silent change, at the first position of codon 11, was introduced by misincorporation of dGMP opposite T at +72, using a 15-base oligonucleotide complementary to positions +73 through +87. Of ten plaques chosen at random and having identical wild type blue color, the DNA of five had the desired silent base change.

TABLE 2

Efficiency of Mutagenesis with Uracil-containing M13mp2 DNA

| Experimental Condition | ung⁻ transfection Total PFU | Mutants | % | ung⁺ transfection Total PFU | Mutants | % |
|---|---|---|---|---|---|---|
| Sham primed | 1492 | 2 | 0.13 | 1 | 0 | — |
| Primed, uncopied | 2180 | 42 | 1.90 | 0 | 0 | — |
| Copied, no ligase | 2715 | 24 | 0.88 | 234 | 2 | 0.85 |
| Copied + ligase | 3695 | 248 | 6.70 | 1157 | 589 | 51.0 |
| Copied + ligase + glycosylase | 256 | 136 | 53.0 | 277 | 145 | 52.0 |
| Copied + ligase* + glycosylase + alkali | 26 | 21 | 81.0 | 38 | 34 | 89.0 |

*The decrease in biological activity associated with this treatment could result from several factors including decreased efficiency of transfection of complementary strands or single-stranded versus double-stranded DNA, or damage due to alkali treatment.

TABLE 3

Efficiency of Site Specific Mutagenesis Using Different Protocols

| Mutation | Complementary strand Bases | Complementary strand Phenotype | Viral strand mutant Phenotype | Viral strand mutant Selection | Percent mutants | Sequence Analysis |
|---|---|---|---|---|---|---|
| Protocol 1 - Oligonucleotide-directed mutagenesis with selection | | | | | | |
| C → G | 15 | blue | light blue | blue | 40.0 | 4/4 |
| Protocol 2 - Misincorporation Mutagenesis with selection | | | | | | |
| C → A | 17 | blue | blue | colorless | 53.4 | 5/5 |
| Protocol 3 - Misincorporation mutagenesis without selection | | | | | | |
| C → T | 17 | blue | blue | none | 60.0 | 6/10 |
| T → C | 15 | blue | blue | none | 50.0 | 5/10 |

Protocol 1 The mutation was introduced via the 15-base oligonucleotide (PL Biochemicals) complementary to nucleotides +76 to +90 of the lacZ$_\alpha$ gene in M13mp2. The 5'-OH termini were phosphorylated, and the 15-mer was hybridized at a 2:1 primer to template ratio to a (light blue) mutant M13mp2 template containing a C at position +82, thus creating a C:C heteroduplex. Synthesis was performed as described in the legend to Table 1 but at 0° for 15 min. followed by 16° for 120 min.

Protocol 2 Wild type (blue) uracil-containing M13mp2 template was primed with a 17-mer (P.L. Biochemicals) complementary to nucleotides +59 to +75 of the lacZ$_\alpha$ coding region. The desired site-specific change, a C → A change at position +58, was created by misincorporating a T opposite a template C [a C(+):T(−) mismatch]using the error-prone avian myeloblastosis virus polymerase and dTTP only. Reactions were performed as follows: To a 25 μl volume containing the oligonucleotide primed DNA (0.5 μg), 20 mM Hepes (pH 7.8), 10 mM MgCl$_2$, and 500 μM dTTP, were added 4 units of AMV DNA polymerase (life Sciences, Inc.). After 10 min at 37°, the remaining three dNTPs were added to 500 μM and incubation at 37° was continued for 5 min. The final additions were dithiothreitol to 2 mM, rATP to 200 μM, 5 units of T4 DNA ligase, and 0.5 unit T4 DNa polymerase (P.L. Biochemicals). Incubation was at 37° for 60 min, and thereactions were terminated by adding EDTA to 15 mM.

Protocol 3 The C → T change was produced as described in Protocol 2, except that misincorporation of A opposite C at +58 was produced using AMV polymerase and dATP only. While this experiment was performed without visual selection for plaque color, a later re-examination of the plates containing the mutant plaques showed that this change unexpectedly resulted in a very slight decrease in blue color intensity. The T → C change at position +72 was introduced using a 15-base oligonucleotide (Bethesda Research Laboratories) complementary to positions +73 to +87, AMV polymerase and dGTP only. As expected, this mutation was silent.

In all cases, the unfractionated products of the reactions were used to transfect competent ung⁺ host cells, which were then plated.

I claim:

1. A process for producing site-specific mutageneis in genes comprising the steps of:
    (1) Separating the strands of a DNA molecule that encodes a peptide;
    (2) Replacing thymine with uracil in one strand of the DNA from step (1);
    (3) Preparing a single-stranded DNA fragment that contains one or more mismatched nucleotides and that will hybridize to the uracil-containing DNA strand prepared in step (2);
    (4) Hybridizing the uracil-containing strand prepared in step (2) to the strand of DNA fragment prepared in step (3) to form a heteroduplex;
    (5) Converting the heteroduplex formed in step (4) to a full-length double-stranded DNA molecule; and
    (6) Hydrolyzing the uracil-containing strand by in vitro treatment with uracil-glycosylase or by inserting the product of step (5) into a ung+ E. coli.

2. A method of claim 1 wherein the hydrolysis of the uracil-containing strand results from in vitro exposure to glycosylase.

3. A method of claim 1 wherein the hydrolysis of the uracil-containing strand results from insertion of the full-length double-stranded DNA molecule of step (5) of claim 1 into a ung+ E. coli.

4. A method of claim 1 wherein the uracil-containing template is produced in E. coli dut⁻ung⁻ cells.

* * * * *